United States Patent [19]

Danielsson et al.

[11] 4,223,387
[45] Sep. 16, 1980

[54] DEVICE FOR EXAMINATION OF DISTANCES IN A PICTURE

[76] Inventors: Per-Erik Danielsson, Hedborns Gata 30, S-582 49 Linköping, Sweden; Carl A. B. Kruse, Kindlyckevägen 9, S-590 41 Rimforsa, Sweden

[21] Appl. No.: 972,640

[22] Filed: Dec. 22, 1978

[30] Foreign Application Priority Data

Jan. 20, 1978 [SE] Sweden ............................. 7800736

[51] Int. Cl.$^2$ .................. G06F 15/46; G06K 9/12
[52] U.S. Cl. .................................... 364/515; 364/489
[58] Field of Search ............... 364/515, 561, 489, 490, 364/491; 340/146.3 E, 146.3 MA

[56] References Cited

U.S. PATENT DOCUMENTS

| | | | |
|---|---|---|---|
| 3,609,307 | 9/1971 | Totsuka et al. | 364/561 X |
| 3,893,080 | 7/1975 | Ho et al. | 340/146.3 E |
| 3,905,018 | 9/1975 | Gray | 340/146.3 MA |
| 3,909,602 | 9/1975 | Micka | 364/490 |
| 4,003,024 | 1/1977 | Riganati et al. | 340/146.3 MA X |
| 4,109,237 | 8/1978 | Hill | 340/146.3 E |
| 4,138,662 | 2/1979 | Shimoyama | 340/146.3 MA |

Primary Examiner—Edward J. Wise
Attorney, Agent, or Firm—Seidel, Gonda, Goldhammer & Panitel

[57] ABSTRACT

A device examines a two dimensional quantized picture to determine whether any objects are closer together than a set minimum distance. The quantized picture has incremental areas assigned values of 0 or 1 corresponding to the presence or absence of an object. An array of interconnected logical cells identifies the presence of a separate object in the picture. The dimensions of the array correspond to the acceptable minimum distance between objects.

The device may be used to inspect for insufficient conductor separation or unacceptably wide conductors in printed circuit boards.

1 Claim, 22 Drawing Figures

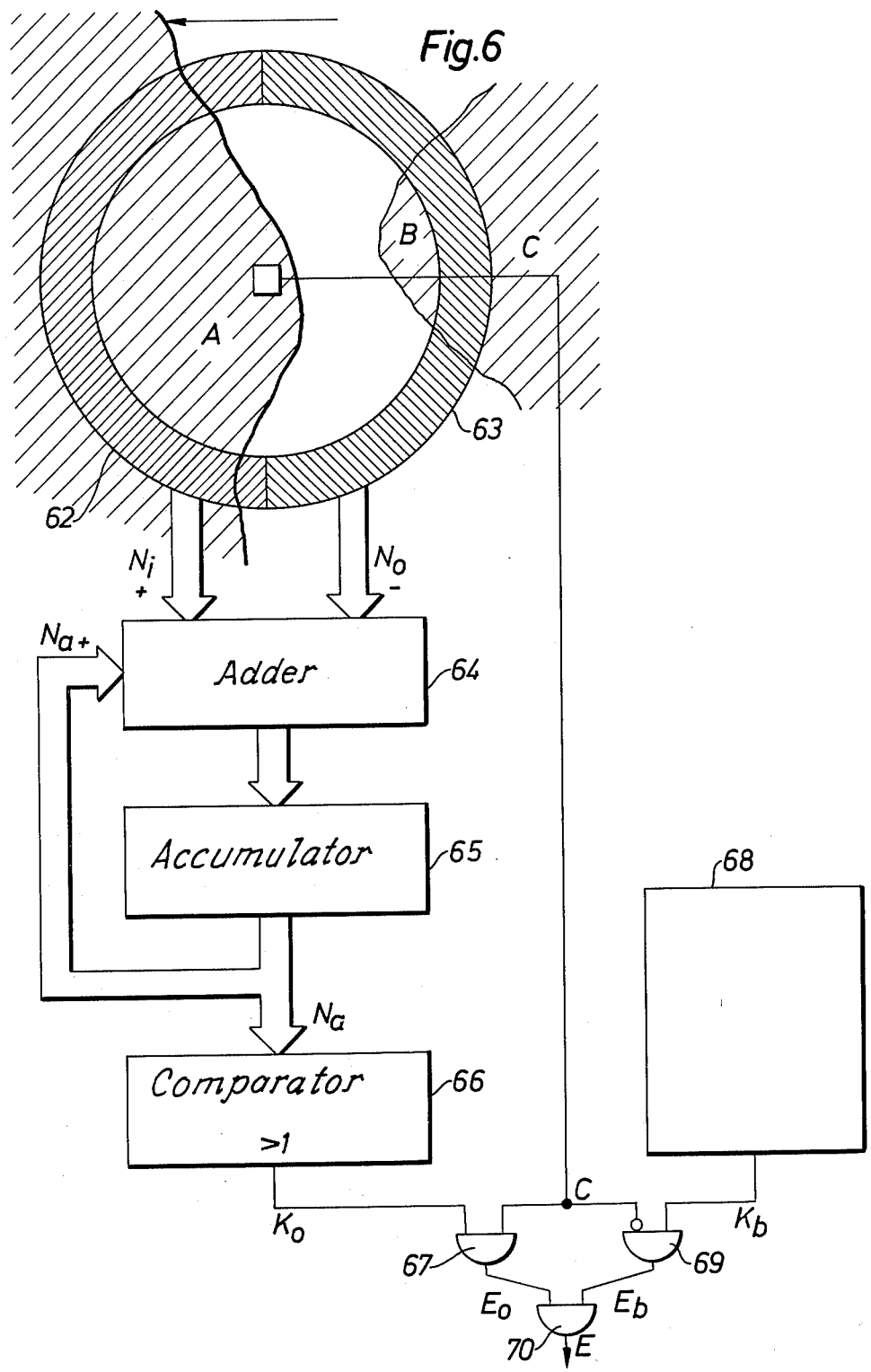

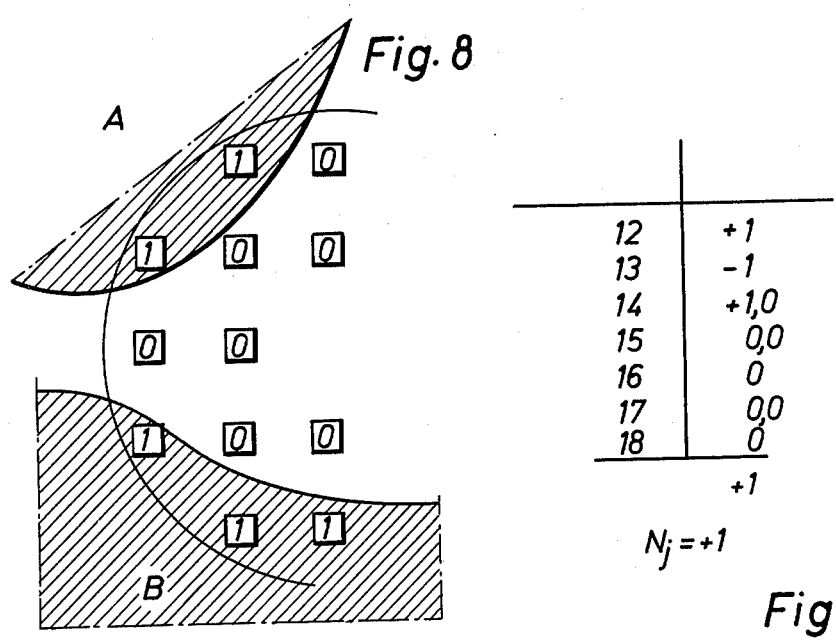
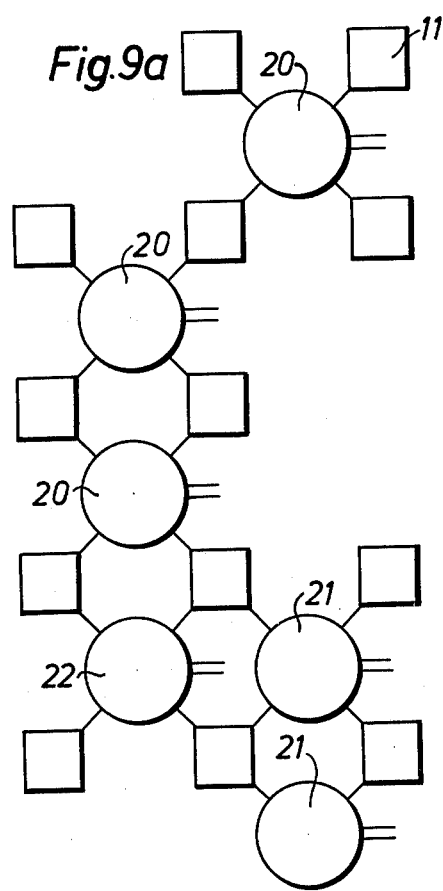
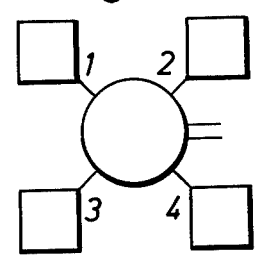
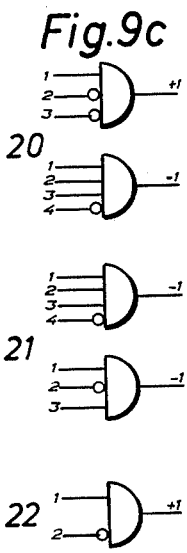

DEVICE FOR EXAMINATION OF DISTANCES IN A PICTURE

The present invention relates to a device for examination of distances in a picture. Specifically the invention relates to a device for examination of distances between objects in a two-dimensional, quantized picture where the individual picture elements, or points, have the value 0 or 1 and objects consist of contiguous elements that have the same value.

The invention can be used, for example, to perform automatic inspection of printed circuit boards in the electronic industry. Present-day methods for finding defects in the printed conductor pattern are extremely labor-intensive. Common defects are insufficiently wide conductors and insufficient conductor separation. A device employing the principles of the invention described herein can detect and call attention to both of these defects.

The invention is also usable in every other application involving the examination and inspection of distances between objects in a two-dimensional picture that has been quantized, i.e. digitized, according to the above principles. This digitizing can occur, for example, in the scanning of the object to be depicted in a scanner, whose resulting serial digitized information is stored in long shift registers that are read out in parallel during the inspection process. A method according to this principle is described, for example, in U.S. Pat. No. 3,832,687. This method requires that a digitized representation of the entire two-dimensional picture be first created and stored in registers, from which information is then read during the examination process. Another method employs an array of sensors, resembling the human retina, to read and digitize in parallel the information required at each step of the examination process.

The present invention originates from research in the area of picture processing by computer. The literature describes various algorithms which relate to the problem solved by this invention: computation of the Euler number, shrinking and expansion, etc. Labelling of objects is a well-known standard procedure for distinguishing one object from another.

A description of a computer intended for picture processing was published in "The Illinois Pattern Recognition Computer—ILLIAC III", IEEE Trans. Electron. Comput., EC-12, No. 5, 1963, pp. 791-813. ILLIAC III is a general-purpose machine for picture-processing applications, and would require, in order to perform the complete function as performed by the present invention, a program and various supplementary data such as masks and intermediate stored results.

The information processing performed by the present invention can of course by performed by any computer. All such implementations, including those mentioned above, have the disadvantage that this processing cannot be realized in hardware but instead requires a program of some sort. A consequence of this, in the application of printed-circuit inspection, is intolerably long inspection times.

The object of the present invention is thus the realization of a device for inspection and examination of distances between objects in a two-dimensional digitized picture, in such a form that the device contains only basic digital logic components and processes picture information without the use of a computer program. A device of this type is described in Swedish Patent Application No. 77 01565-9. That device, however, differs in its fundamental principles from the present invention.

Devices comprising only basic digital logic elements (AND-gates, OR-gates etc.) in connection with picture processing are known per se. Such devices are described for instance in U.S. Pat. No. 3,859,633, 3,893,080 and 4,015,240. These patents describe systems for identifying finger prints. Such systems, however, are useless in connection with examination of distances between objects.

The object mentioned above is according to the invention solved by a device in accordance with the attached patent claims.

A device constructed according to the principles of the present invention has a speed that exceeds the speed realizable with a general-purpose computer by several orders of magnitude.

The following more detailed explanation of the present invention and its various implementations makes reference to FIGS. 1-12, in which:

FIG. 6 shows schematically how the number of objects inside a test circle can be counted;

FIG. 7 shows (a) how memory cells are connected to logical cells for detection of incoming objects, (b) a typical logical cell with its surrounding memory cells, (c) the construction of different logical cells, (d) the circuit for producing the arithmetic sum, and (e) the adding circuit 19a;

FIG. 8 shows a specific example of the computing in the embodiment according to FIG. 7;

FIGS. 9a–9c show another embodiment where diagonally adjacent elements are not considered as being connected;

Figure 1:
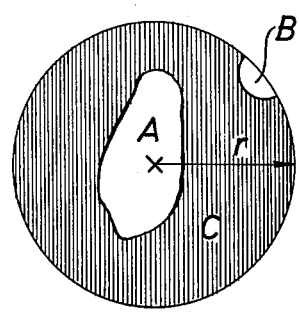
FIG. 1 shows the basis of the present invention in schematic form.

FIG. 1 shows the basis for the present invention. The figure shows two objects, denoted A and B, which are separated by a background object denoted C. Objects A and B each occupy an area that can be considered to consist of a number of contiguous picture elements, all of which are assigned the predefined value 0 or 1. The background object C can also be considered to consist of a number of contiguous picture elements, in this case with the opposite value from the elements of objects A and B. Thus, if the points in objects A and B are assigned the value 1, the points in the background object C will have the value 0.

To determine whether the separation between objects A and B is less than a certain distance r, a test circle is placed as shown in the figure. This test circle is one example of the array, or subpicture, that can be used. The points of the circle are sensed, and their values are used to determine whether the circle contains at least one isolated object having the same value as the object which includes the center point of the circle.

After the examination of the subpicture, either the array defining the subpicture is shifted relative to the two-dimensional picture being inspected, or the picture is shifted relative to the array, so that a new subpicture can be examined. This new subpicture has the same geometric form as the first subpicture, but is located elsewhere within the picture under examination, i.e. located so that a different element of the picture under examination is the center point of the subpicture. Examination of the entire picture for distances between objects is performed by allowing each point in the picture to become the center point of a subpicture, for example by means of shifting in both the x and y directions. Thus, the number of tests required to examine a picture is equal to the number of elements in the picture, or expressed in another way, each picture point has an associated subpicture.

It follows from the above explanation that both the case of two objects with value 1 which are less than distance r from each other, and the case of two background objects (objects with value 0) which are less than distance r from each other, will be detected. This latter case is equivalent to testing the width of an object of value 1.

Figure 2:
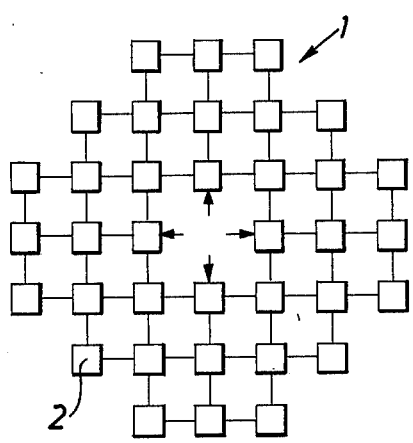
FIG. 2 shows how cells in accordance with the present invention are interconnected for the case in which the picture is digitized using a square grid.

FIG. 2 shows a schematic view of a device 1 that consists of a number of cells 2 for each picture point in the subpicture except for the center point. Between the cells 2 signals are transferred in both directions. In the center a constant signal (for instance logical 1) is initiated for propagation from the center to the periphery of the subpicture.

The discrete circle of FIG. 2 is just an example of a possible geometric form for the subpicture. The function realized in this case is that of a distance test which is independent of orientation. In some cases it can, however, be desirable for the minimal allowed distance to be different in different directions. Thus, spatially discrete subpictures of elliptical, square, rectangular, rhomboidal, hexagonal, and other forms can be of interest. Furthermore, from the detailed description below it is clear that the picture point that here is denoted the center point not necessarily has to lie in the center of the subpicture, but only has to be an inner point of the subpicture.

Figure 3:
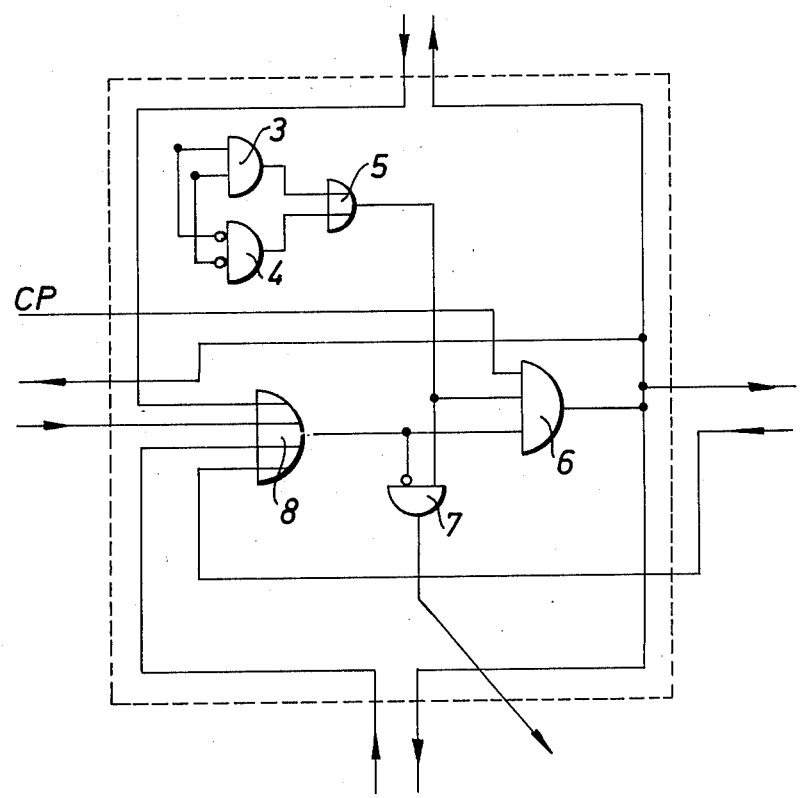
FIG. 3 shows the construction of a cell intended for use with a square grid.

FIG. 3 shows a first embodiment of the logical cell 2 used in the device 1 representing an implementation of the present invention. As is evident from the figure, the cell 2 contains only basic logical elements, i.e. AND gates and OR gates. Each logical cell 2 in the device 1 senses the value of the center point of the subpicture. This value is applied to an input of an AND gate 3. Simultaneously each logical cell 2 senses the value of a point in the subpicture associated with that particular cell. This value is applied to the other input of AND gate 3. AND gate 3 is also supplied with a clock pulse signal CP that resets the device after each test. If we assume that the center point of the subpicture has the value 1, then AND gate 3 will give a logical 1 if the point associated with the cell has the value 1. The cell also contains AND gate 4, to which the values of the center point and of the associated point are applied in inverted form (denoted by the small circles at the inputs of the AND gate). Thus, AND gate 4 gives a logical 1 in the case where both the center point and the point associated with the cell have the value 0. From the foregoing it should be evident that OR gate 5 will give a logical 1 in the case where the picture point associated with the cell has the same value as the center point, regardless of whether that value is 0 or 1. If the associated point does not have the same value as the center point, OR gate 5 will give a logical 0. The output signal from OR gate 5 is fed to an AND gate 6. The output from AND gate 6 is then fed to all adjacent logical cells. Similarly, the cell 2 receives the output signals from the corresponding AND gates 6 of the adjacent cells. These received signals are applied to the inputs of an OR gate 8, whose output signal drives another input of AND gate 6. Thus, one observes that AND gate 6 will give a logical 1 only in the case where the center point has the same value as the picture point associated with the cell. However, this condition is not sufficient. Simultaneously it is necessary that AND gate 6 receives a logical 1 from at least one of the neighbour cells. However, a necessary condition for such a signal is that the picture point associated with said neighbour cell 2 also has the same value as the center point. One may thus infer that logical 1's will propagate outward from the center of FIG. 2 until, for example, the edge of object A in FIG. 1 is encountered.

From the above description it should be evident that the device 1 will always propagate a logical 1 outward from the center element, independent of the value of said center element. Note that no logical cell 2 is associated with the center point; instead the constant value logical 1 is propagated outward regardless of the actual value of the center point.

The picture elements located between objects A and B (i.e. those of object C) do not have the same value as the center point. Thus, these points will block the outward propagation of logical 1's, so that these 1's will not reach the cells associated with the elements of object B. In these latter cells, OR gate 5 will generate a logical 1 (since the elements of object B have the same value as the center point), but the output of OR gate 8, and hence the second input of AND gate 6, will be logical 0 since no 1's are received from the cells associated with object C. This condition can be recognized by inverting the output signal from OR gate 8 and applying it, together with the output from OR gate 5, to an AND gate 7. In the situation just described, AND gate 7 will give a logical 1, which indicates that objects A and B are too close to each other. Equipping each logical cell 2 with this AND gate 7, and connecting all the output signals of these AND gates to an OR gate, completes the device 1. With this configuration it is sufficient that only one of the AND gates 7 give a 1 output for the device to give an error indication. This extreme case corresponds to the existence, somewhere in the subpicture, of an isolated "one-point object" having the same value as the center point.

Each logical cell thus gives logical 1 from AND gate 7 in the case where the picture element associated with the cell has the same value as the center element, but where the associated element is not part of the same object as the center point. The device 1 then gives a warning signal.

The double interconnections between cells give rise to closed loops of logical signals and thus bistable configurations in the cell array. These loops must be broken by means of a logical 0 on clock signal CP after each test (the number of tests being equal to the number of subpictures or the number of picture elements in the picture).

Figure 4:
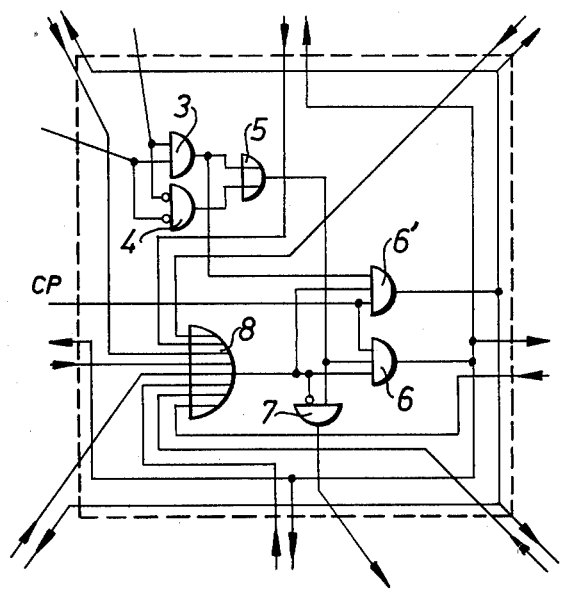
FIG. 4 shows the construction of a cell intended for use with a square grid, but which also takes consideration of diagonally adjacent elements.

If the objects in the picture are very narrow, only one picture element in width, it may be desirable for two points to be considered to be part of the same objects even if they are only diagonally adjacent. In this manner, very narrow objects will be properly treated independent of their orientation. In this case the cells 2 of the device 1 may be of the type shown in FIG. 4. In FIG. 4 the components whose functions correspond to the functions of corresponding components in FIG. 3 have been denoted with the same reference designations. In order to avoid logical contradictions, only objects consisting of elements with value 1 are allowed to have points that are only diagonally adjacent. Objects consisting of elements of value 0 will be considered connected only if their elements are adjacent in one of the four main directions of FIG. 3. Thus, in FIG. 4 the output of gate 3 is used as a condition for propagating signals diagonally by means of AND gate 6'. Propagation outward from the center of the array is initialized with logical 1 as in FIG. 2, with the addition that the cells diagonally adjacent to the center point are initialized with logical 1 only if the value of the center point is 1. If it is desired to implement the above diagonal connectivity for the symmetrical case of objects of points with value 0, the input from AND gate 6' must be driven from the output of AND gate 4 instead of AND gate 3, and the cells diagonally adjacent to the center point must be initialized with logical 1 only if the center point has the value 0.

Figure 5:
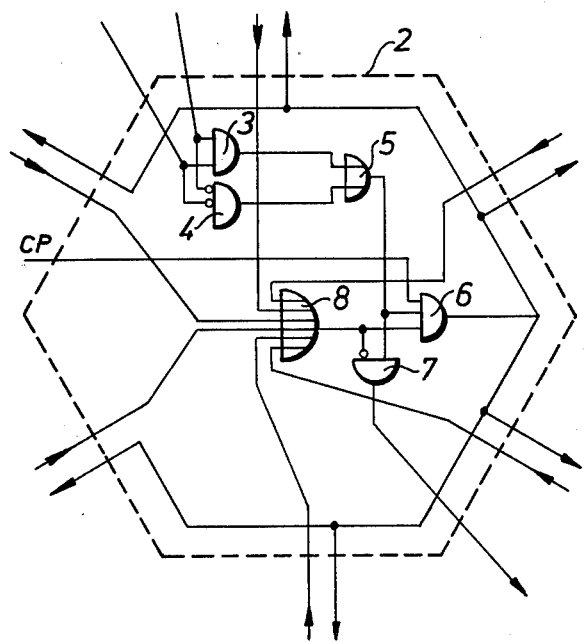
FIG. 5 shows the construction of a cell intended for use with a picture that is digitized using a hexagonal grid.
Figure 7A:
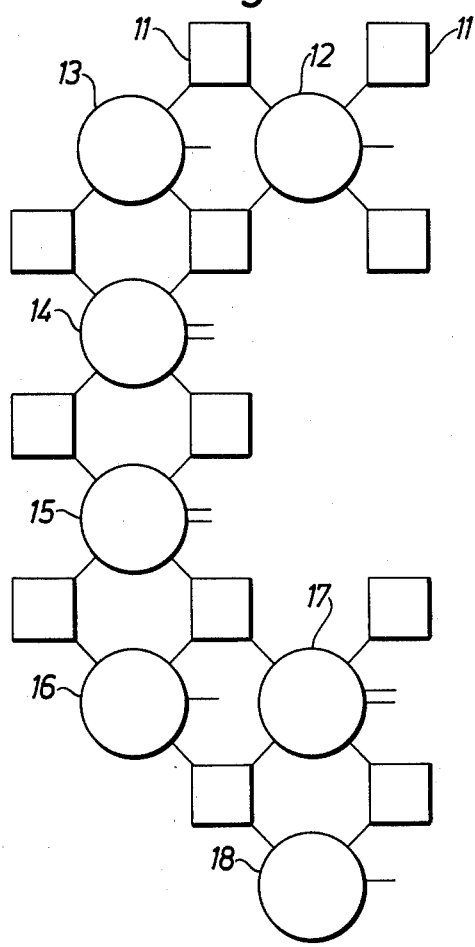
Figure 7B:
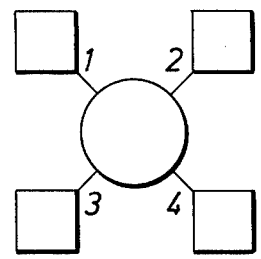
Figure 7C:
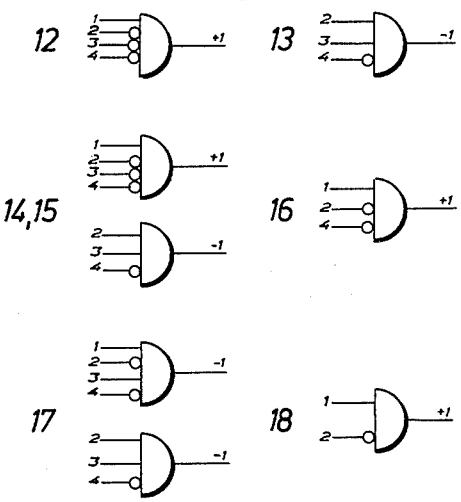
Figure 7D:
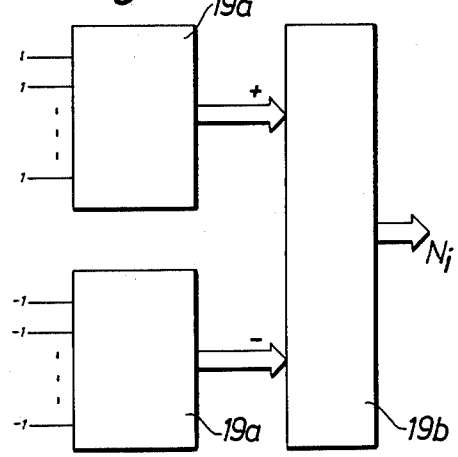
Figure 7E:
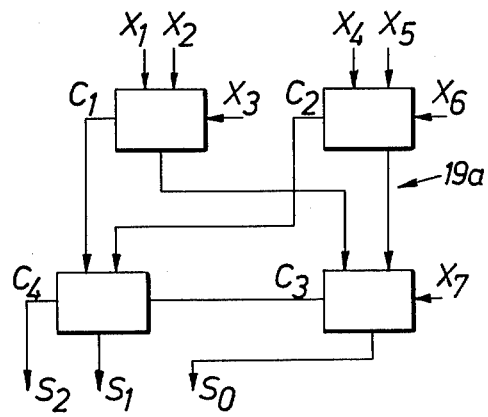

FIG. 5 shows an embodiment of a logical cell 2 in a device 1 intended for a hexagonal array of picture elements. This logical cell is identical to the cell of FIG. 3, except that OR gate 8 now has six inputs, one from each adjacent cell.

If a more precise measurement of the minimal distance between the center point and another object is desired, the warning signal outputs from the individual cells can be organized in groups correspondingly to circular rings of the picture elements around the center point. The signals from the cells in each ring are then fed to separate OR gates, one such gate for each ring.

As mentioned above, the subpicture can, for examination of different orientation-dependent distances, have other shapes than the approximately circular form discussed here.

Furthermore, the signal propagation between cells can be allowed to occur over an area larger than that examined for inter-object distances. For example, the warning-signal outputs from all the cells 2 within a radius $r_1$ from the center point can be fed to an OR gate. Additional cells 2 can be added to the device so that the entire subpicture has radius $r_2$, with $r_2$ greater than $r_1$. In this case one does not use the output signals of these latter cells, but only their propagating function. Expansion of the device 1 in this manner prevents, for example, the erroneous identification of a sharp corner as two separate objects. Since the propagation of logical 1's continues sufficiently far, the device will recognize that the situation is one of a single continuous object, and no warning signal will be given.

The above described test to determine whether there further to an object A, that lies over the center point, exists at least one object B separated from object A and having the same picture element value as object A, can also be done incrementally by determining the number of incoming and outgoing objects.

In FIG. 6 there is shown schematically how the incremental counting of the number of objects can be performed. Around the periphery of the test circle there are arranged logical nets 62 and 63, which nets are arranged in such a way that the number of objects that enter the test circle as it moves over the point pattern in the direction of the arrow is detected by net 62, while the number of objects that leave the test circle are detected by net 63. The construction of the logical nets 62 and 63 will be described in detail below. It should be noted that the nets do not count the number of picture points with value 1 or value 0, but rather the number of contiguous objects. The difference in each moment between the number of detected objects in net 62 and net 63 represents the number of objects enclosed by the test circle. By means of an adder 64 and an accumulator register 65 the net number of entering objects $N_i-N_o$ is determined and added to the number of objects $N_a$ already stored in the accumulator. The new $N_a$ value formed in this way represents the number of objects within the test circle in its new location.

This continuously determined number of objects $N_a$ is supplied to a comparator 66, the binary outsignal of which expresses whether $N_a>1$ or not. Thus, this signal indicates whether there is more than one subject within the test circle ($N_a>1$). If the number of objects with the same picture point value is greater than 1 and simultaneously the center point is lying within one of the objects, which is indicated by the signal C having the logical value 1, an error shall be indicated since the distance between the objects must be too small.

The error signal $E_0$ is formed as the logical product of the value C of the center point and the value $K_0$ of the output signal of the comparator in AND gate 67. It is evident that a corresponding distance test can also be performed on the background pattern (objects with picture element 0) in a similar logical net 68. In order to indicate errors $E_b$ it is necessary in this case that the output $K_b$ of net 68 indicates that more than one "background object" lies within the test circle, and that the center point belongs to the background objects, i.e. that C has the logical value 0. The error signal $E_b$ is formed as the logical product of C' and $K_b$ in AND gate 69 and expresses an error in the background pattern within the test circle. Finally, in FIG. 6 there is shown how an error signal E, indicating error in both objects and background, is formed in OR gate 70 by logical addition of error signals $E_0$ and $E_b$.

FIG. 7 shows an embodiment of net 62 in FIG. 6. On the periphery of the digitized test circle there are memory cells 11 containing the picture element values along the two circles lying nearest the edge of the test circle. As the test circle is moved over the pattern these memory cells take the values of picture points corresponding to the new location of the test circle. A number of logical cells 12, 13, ..., 18 are supplied with the values of the surrounding memory cells, as is indicated in a typical case in FIG. 7b. The construction of the logical cells is shown in FIG. 7c. These cells consist of one or more AND gates, the outputs of which are associated with the values $+1$ and $-1$ (in accordance with FIG. 7c) when the output signals have the value logical 1. Otherwise the outputs are associated with value 0. These outputs are fed to the addition/subtraction net 19, in which the arithmetic sum $N_i$ of the input signals is formed. This sum $N_i$ expresses in each moment the number of objects entering the test circle. In FIG. 8 there is shown a case with one incoming object A and an object B already present within the circle. The arithmetic sum $N_i$ of the outputs of the gates is in this case +1. FIG. 7e shows an embodiment of the adding circuit 19a mentioned above. The units denoted FA are full adders forming the arithmetic sum of their three binary inputs. In the figure there is shown an example for summing seven binary inputs $x_1, x_2, \ldots, x_7$. From the upper row one receives partial sums and carry signals that are finally added in the lower row of the full adder. The outsignals $S_0$, $S_1$ and $S_2$ represent the binary coded result of the summing process.

The test mentioned above can be amplified by making the comparator 66 of FIG. 6 produce an error signal when $N_a \neq 1$ instead of $N_a > 1$. In this case also small defects that are negligible in certain cases will be detected (for instance ring shaped objects with a radius smaller than the radius of the test circle).

The embodiment shown in FIG. 7 can be modified in several ways, since the principles described above can also be used in a mirror version, i.e. inputs 1, 3 and 2, 4 are interchanged on all logical cells.

The embodiment of FIG. 7 is based on an object definition that considers two diagonally adjacent picture points as connected. In FIG. 9 there is shown another embodiment where diagonally adjacent picture points are considered as belonging to separate objects. The logical content of the cells differs from the embodiment of FIG. 7, but the adding/subtracting unit 19 is the same.

Figure 10A:
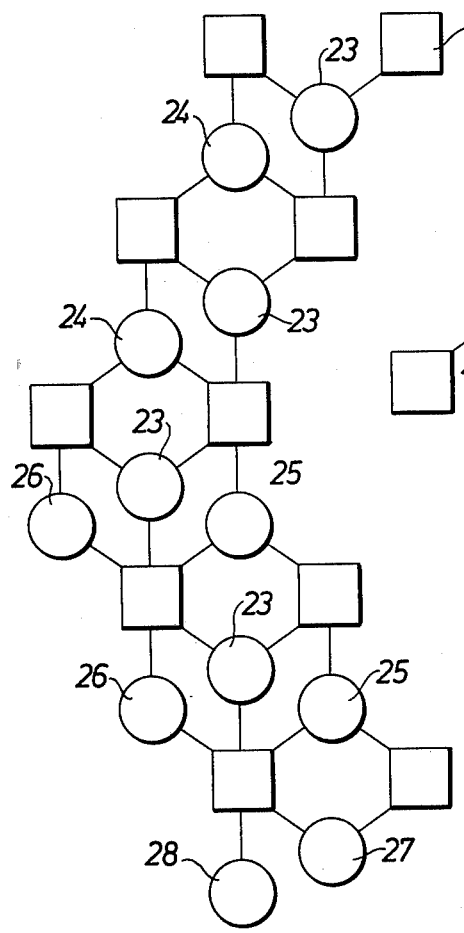
FIGS. 10a–10c show an embodiment, in which the digitizing is made in a hexagonal pattern.
Figure 10B:
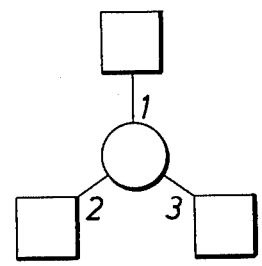
Figure 10C:
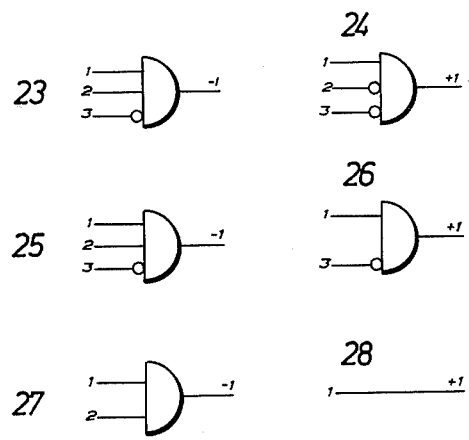

As an alternative to the rectangular digitizing pattern there is shown in FIG. 10 another ambodiment in which the picture points form a hexagonal pattern.

It is noted that the logical net 63 in FIG. 6 is a mirror version of the logical net 62, and hence a detailed description is not necessary.

Figure 11A:
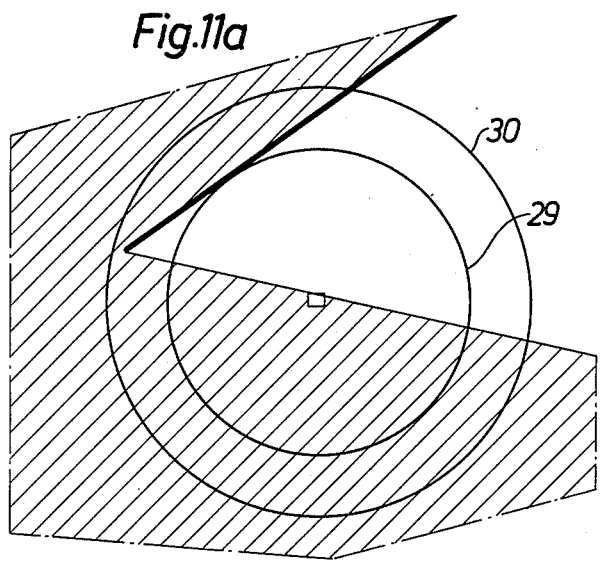
FIG. 11 shows schematically three different cases (a), (b) and (c) where two concentric detection circuits have been combined.
Figure 11B:
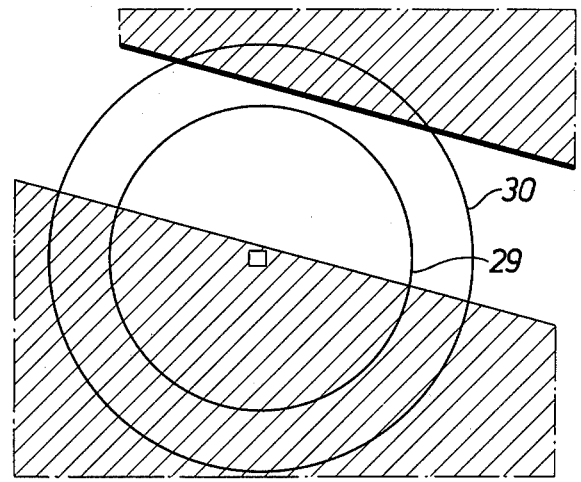
Figure 11C:
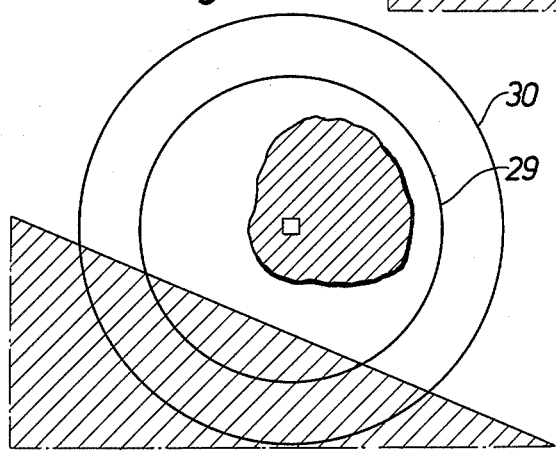
Figure 12:
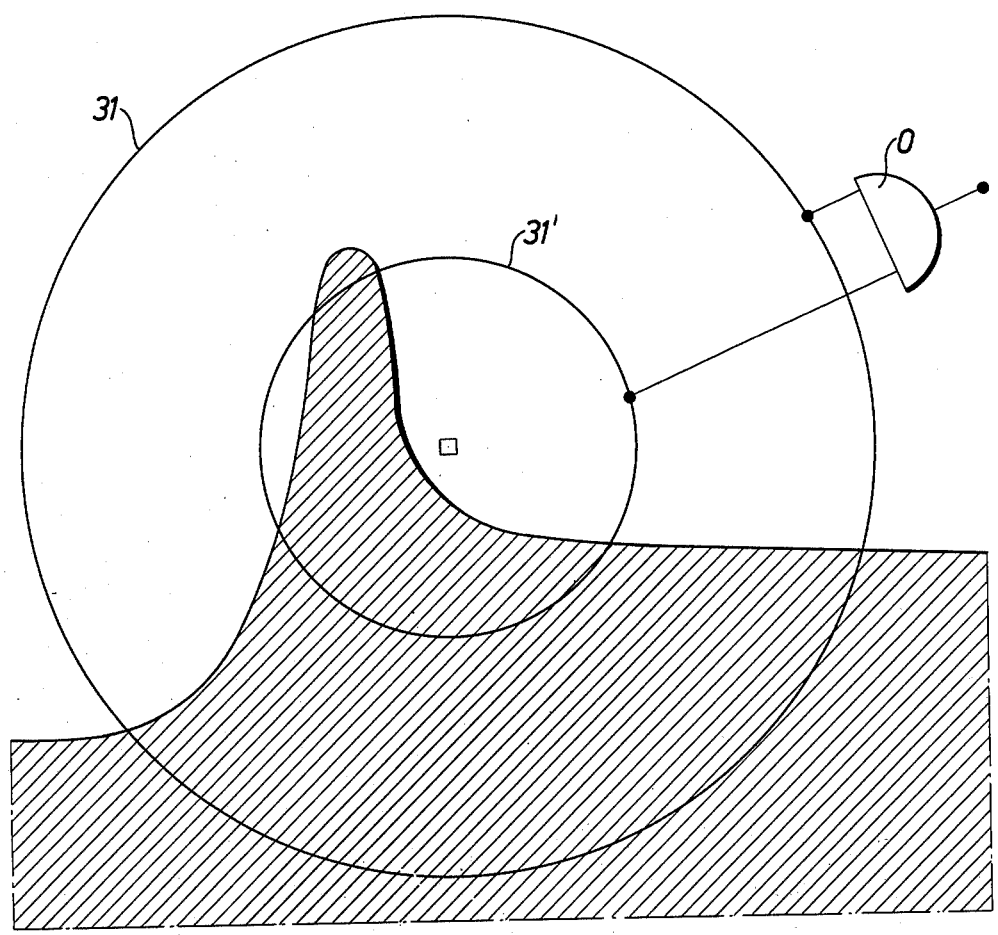
FIG. 12 shows another way to combine the detection circuits.

Furthermore, several test regions enclosing each other can be used. The error signals from test circles of different size can together form composite error signals. For instance, the error indication in connection with sharp corners can be partially avoided, since an error is only indicated if errors are indicated for several test circles. This fact is illustrated in FIG. 11a, where two devices 62, 63, 64, 65 and 66 as in FIG. 6 sense the picture points on one double periphery 29, 30 each and produce one signal $K'_0$ and $K''_0$, respectively. The two signals are combined in a logical AND gate so that the logical signal "$K'_0$ AND $K''_0$" is formed. This composite signal is fed, as signal $K_0$ in FIG. 6 to the final error detecting net 67, 69 and 70. It is evident that an error is indicated only if both signals $K'_0$ and $K''_0$ have the logical value 1. In the case of the sharp corner of FIG. 11a no error will be indicated. The minimum allowed angle is determined by the radii of circles 29 and 30. The conditions in FIG. 11b are such that only the outer test circle indicates an error which is not sufficient for a composite error indication. Thus, the composite device does not indicate an error. For the objects in FIG. 11c there will be an error indication, since both the outer and inner test circle will indicate an error. FIG. 12 shows another logical interconnection of output signals of two test circles 31, 31' lying within each other. In this case these output signals have been connected to an OR gate 0. Such an interconnection is suitable if one desires to detect also short protrusions of an object. In this case the critical distance is the radius of the bigger test circle. Thus, the inner test circle will in all normal situations have no influence on the output signal of OR gate 0, since too small distances between big objects already have been detected by the larger test circle 31. However, if one is interested in detecting also short protrusions from objects test circle 31 would in this case be insufficient, since there are only two objects within that circle, and these two objects have different values. By introducing also a test circle 31' with a smaller radius such protrusions will be detected, since the smaller test circle 1' will "see" two background objects of the same kind with insufficient separation therebetween. It is evident that the closed test loops according to FIGS. 11 and 12 need not necessarily be concentric, but can be displaced to each other and have different geometric form. Furthermore, it should be noted that the invention is not restricted in interconnection of two loops, rather the number of loops can be bigger than two. Furthermore, it is noted that the interconnection of loops is not restricted to the use of AND gates or OR gates, but that other combinations of these or other logical elements can be of interest. Hereby a warning signal can be obtained from the apparatus according to the invention also for one or several combinations of loop output signals. With the concept warning signal or error signal is intended not necessarily a signal indicating an error but only a signal indicating that the distance between two objects is lying under a predetermined value. Finally it is noted that the apparatus can be modified in several ways within the scope of the present invention, which is only restricted by the attached patent claims.

What we claim is:

1. Apparatus for examining a two-dimensional quantized picture of an area to determine whether there exists within the area any objects which are closer than a pre-determined acceptable minimum distance from each other, said picture comprising discrete picture elements each of which represents a unit of said area, each picture element being assigned either a value of logical 1 when an object occupies any part of a corresponding unit of area, or a value of logical 0 when no object occupies any part of said corresponding unit of area, comprising:
    (a) an array of interconnected logical cells for scanning said picture in a sequence of uniform sub-pictures, each of said sub-pictures having dimensions related to the minimum distance allowable between objects in the quantized picture;
    (b) means associated with said array for determining the number of objects within a sub-picture at any time;
    (c) means for generating a warning signal when the number of objects inside a sub-picture is greater than one.

2. Apparatus for examining a two-dimensional quantized picture of an area to determine whether there exists within that area any objects which are closer than a pre-determined acceptable minimum distance from each other, said picture comprising discrete picture elements each of which represents a corresponding unit of said area, each picture element being assigned either a value of logical 1 when an object occupies any part of object a corresponding unit of area, or a value of logical 0 when no object occupies any part of said corresponding unit of area, comprising:
    (a) an array of interconnected logical cells, said array corresponding to a sub-picture of said quantized picture, said sub-picture having a geometric shape and size related to the minimum acceptable distance between objects;

(b) a first cell of said logical cells of the array corresponding to a picture element at a pre-determined reference position within said sub-picture, said first logical cell comprising means for generating a logical propagation signal equal to the logical value of the picture element occupying said reference position;

(c) each of the others of said logical cells in said array comprising: (i) means for comparing the logical value of the picture element corresponding to each said other cell to the logical value of the logical propagation signal produced by the first logical cell, (ii) means for producing said logical propagation signal when the logical value of the picture element corresponding to each said other logical cell is the same as the value of the logical propagation signal of said first logical cell and at least one adjacent cell in the array is also producing said logical propagation signal, (iii) means for producing a warning signal when the logical value of the other picture element corresponding to each said other logical cell is the same as the value of the logical propagation signal of said first logical cell and no adjacent cell is producing said logical propagation signal, 3. Apparatus as in claim 2, wherein each of said other logical cells comprises:
(a) a first AND gate (3), receiving as one input a logical signal having a logical value assigned to the discrete picture element corresponding to said other cell and having as a second input a logical signal having the logical value assigned to the reference picture element;
(b) a second AND gate (4), receiving as one input a logical signal which is the complement of the value assigned to the picture element corresponding to said other cell and having as a second input a logical signal which is the complement of the value assigned to the reference picture element;
(c) a first OR gate (5), receiving as inputs the outputs of the first and second AND gates (3, 4);
(d) a second OR gate (8), receiving as inputs the propagation signals from each adjacent cell;
(e) a third AND gate (6), receiving as inputs the outputs of the first and second OR gates (5, 8), and;
(f) a fourth AND gate (7), receiving as inputs the output of the first OR gate (5) and the inverse of the output of the first OR gate (5) and the inverse of the output of the second OR gate (8).

4. Apparatus according to claims 2 or 3, wherein said first logical cell is located at the center of said array and corresponds to a picture element in the center of the sub-picture.

5. Apparatus according to claim 4, wherein the array is approximately circular in shape.

6. Apparatus according to claim 3, wherein the picture is rectangularly quantized, characterized in that the second OR gate (8) is provided with four inputs.

7. The apparatus of claim 3, wherein the picture is hexagonally quantized, characterized in that the second OR gate (8) is provided with six inputs.

8. Apparatus for examining a two-dimensional quantized picture of an area to determine whether there exists within that area any objects which are closer than a pre-determined acceptable minimum distance from each other, said picture comprising discrete picture elements each of which represents a unit of said area, each picture element being assigned either a value of logical 1 when an object occupies any part of a corresponding unit of area, or a value of logical 0 when no object occupies any part of said corresponding unit of area, comprising:
(a) an array of interconnected logical cells corresponding to a sub-picture of said quantized picture, said sub-picture having dimensions related to the minimum distance allowable between objects in the quantized picture, said array being divided into a first net for recording objects entering the sub-picture and a second net for recording objects leaving the sub-picture as the sub-picture;
(b) means in said first net for producing a first logical signal for each object that enters the sub-picture;
(c) means in said second net for producing a second logical signal for each object that leaves said sub-picture;
(d) means for adding and accumulating said logical signals to indicate the number of objects inside the sub-picture at any time;
(e) means for generating a first warning signal when the number of objects inside the sub-picture is greater than one.

9. An apparatus as in claim 8, wherein:
(a) said sub-picture is approximately circular;
(b) said first net comprises a cluster of logical units receiving input signals corresponding to the logical values assigned to picture elements located in a first half-circular peripheral band of said sub-picture, and;
(c) said second net comprises a cluster of logical units receiving input signals corresponding to the logical values assigned to picture elements located in a second half-circular peripheral band of said sub-picture;

10. Apparatus according to claim 9, further comprising:
(a) means for sensing whether an object lies in the center of the sub-picture;
(b) means for producing a second warning signal when said first warning signal is being produced and there is simultaneously an object in the center of the sub-picture.

11. Apparatus according to claim 10, further comprising:
(a) means for producing a third warning signal when the first warning signal is being produced and there is simultaneously not an object in the center of the sub-picture.

12. Apparatus for examination of the width of an object in a 2-dimensional quantized picture, said picture comprising discrete picture elements each of which represents a unit of said area, each picture element being assigned either a value of logical 1 when an object occupies any part of a corresponding unit of area, or a value of logical 0 when no object occupies any part of said corresponding unit of area, comprising:
(a) a sub-picture having dimensions related to the allowable width of an object in the picture;
(b) nets on the outer peripheries of said sub-pictur, comprising:
(i) a first net for sensing the entrance in the sub-picture of a first zone of contiguous picture elements having a first logical value and for producing a logical signal indicative thereof,
(ii) a second net for sensing the entrance in the sub-picture of a second zone of contiguous picture elements having a second logical value, (iii) a third net for sensing the exit from the sub-picture of said first zone of contiguous picture elements, (iv) a fourth net for sensing the exit from the sub-picture of said second zone of contiguous picture elements, (c) means for adding and accumulating each of said logical signals;

(d) means for generating a first warning signal when the number of said first zones inside the sub-picture is greater than one;

(e) means for generating a second warning signal when the number of said second zones inside the sub-picture is greater than one;

(f) means for sensing whether said first zone lies in the center of the sub-picture;

(g) means for producing a third warning signal when said first warning signal is being produced and there is simultaneously a first zone in the center of the sub-picture;

(h) means for producing a fourth warning signal when the said second warning signal is being produced and there is simultaneously not a first zone in the center of the sub-picture;

(i) means for producing a fifth warning signal when either a third or fourth warning signal is produced.

* * * * *